(12) United States Patent
Kitamura et al.

(10) Patent No.: US 6,628,785 B1
(45) Date of Patent: Sep. 30, 2003

(54) WATER SINKING CONFIRMATION DEVICE AND PORTABLE TERMINAL DEVICE USING THE SAME

(75) Inventors: Toshiyasu Kitamura, Kanagawa (JP); Koichi Yamamoto, Kanagawa (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/439,907

(22) Filed: Nov. 12, 1999

(30) Foreign Application Priority Data

Nov. 12, 1998 (JP) ............................................. 10-322148

(51) Int. Cl.⁷ ............................................... H04M 1/00
(52) U.S. Cl. ........................................ 379/437; 379/451
(58) Field of Search ................................. 379/451, 437; 73/335.01, 73

(56) References Cited

U.S. PATENT DOCUMENTS

| | | | | |
|---|---|---|---|---|
| 4,130,012 A | * | 12/1978 | Lockerby et al. | ............... 73/73 |
| 4,150,570 A | * | 4/1979 | Fuller | ........................ 73/335 |
| 5,224,373 A | | 7/1993 | Williams et al. | |

OTHER PUBLICATIONS

WO 98/23920, International Publication Date: Jun. 4, 1998, Moisture Indicator Label.
XP–002057944, Toppan Printing Co Ltd: "WPI World Patent Information Derwent, GB, Derwent", WPI World Patent Information Derwent, GB, Derwent, vol. 40, Nr. 94.

* cited by examiner

Primary Examiner—Jack Chiang
(74) Attorney, Agent, or Firm—Pearne & Gordon LLP

(57) ABSTRACT

A water sinking confirmation device enabling judgment on whether or not a portable terminal device or the like has been sunk in water. The water sinking confirmation device includes a lower case provided with a hole, a double side coated adhesive member for bonding both sides, surrounding the hole, a transparent sheet for blocking entrance of water from the hole and allowing the state change of a water sinking confirmation seal seen through from the surface thereof, and the water sinking confirmation seal including a double side coated adhesive member disposed at both ends of the transparent sheet and a white plain paper, and the white plain paper applied with red color printing with a water-color ink at the center. The hole is formed at a position not to be covered by another part mounted on the lower case, for example, above a holding member.

18 Claims, 5 Drawing Sheets

WATER SINKING CONFIRMATION DEVICE AND PORTABLE TERMINAL DEVICE USING THE SAME

BACKGROUND OF THE INVENTION

1. Field of the Invention

The present invention relates to a water sinking confirmation device and in particular, it relates to one to be used in a portable terminal device or the like, enabling judgment on whether or not the device has been sunk in water only by seeing a lower case.

2. Description of the Related Art

Conventionally, as a water sinking confirmation device to be used in a portable terminal device such as a portable phone device or a PHS, one shown in FIG. 6 has been known. In FIG. 6, the water sinking confirmation device comprises an internal unit 61 with a water sinking confirmation seal 62 attached at a predetermined position, and a lower case 63 having a hole 64 formed at a predetermined position such that the water sinking confirmation seal 62 attached on the internal unit 61 is seen through a transparent sheet 65, attached together.

However, since other parts of the portable terminal device are mounted on the hole 64 provided in the lower case 63 in the conventional water sinking confirmation device, it involves a problem in that the water sinking state of the water sinking confirmation seal 62 attached on the internal unit 61 cannot be seen directly through the hole 64 formed in the lower case 63.

Moreover, since the water sinking confirmation seal 62 is attached directly on a predetermined position of the internal unit 61 and the transparent sheet 65 is bonded or adhered to the lower case 63, surrounding the hole 64, the water sinking confirmation seal 62 and the transparent sheet 65 are not sealed closely, and thus a problem is involved in that the water sinking confirmation seal 62 may generate the state change when it is not sunk in water.

SUMMARY OF THE INVENTION

In order to solve the above problems, an object of the invention is to provide a water sinking confirmation device enabling judgment on whether or not a portable terminal device or the like has been sunk in water only by seeing a lower case.

In order to achieve the above object, according to the invention, there is provided a water sinking confirmation device comprising: a lower case provided with a hole for confirming water sinking; a double side coated adhesive member for bonding both sides, surrounding the hole; a transparent sheet allowing a state change of a water sinking confirmation seal seen through from a surface thereof; and the water sinking confirmation seal including a double side coated adhesive member disposed at both ends of the transparent sheet and a white plain paper, and the white plain paper applied with red color printing with a water-color ink at a center thereof.

DETAILED DESCRIPTION OF THE PREFERRED EMBODIMENT

Hereinafter, an embodiment of the invention will be described with reference to the accompanying drawings.

Figure 1:
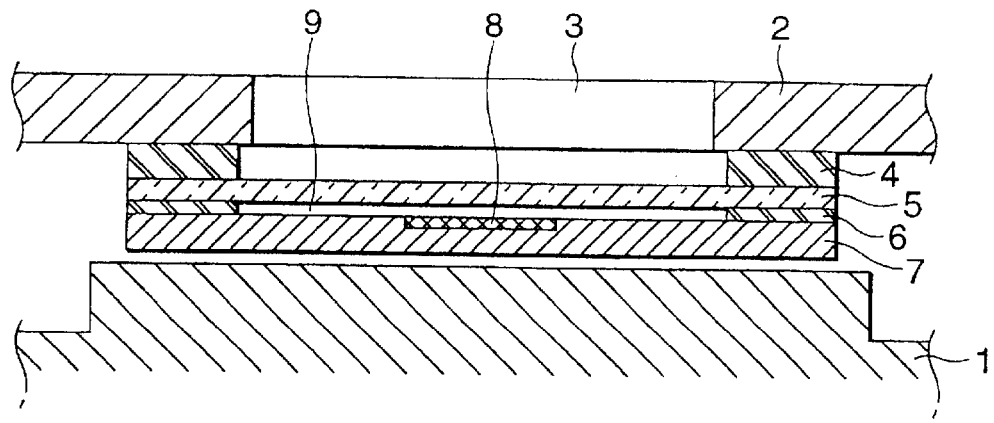
FIG. 1 is a cross-sectional view showing the configuration of a water sinking confirmation device according to an embodiment of the invention.

FIG. 1 is a cross-sectional view showing the configuration of a water sinking confirmation device according to the invention to be used in a portable terminal device, such as a portable phone device or a PHS. In FIG. 1, the water sinking confirmation device comprises a lower case 2 provided with a hole 3, a double side coated adhesive member 4 for bonding both sides, surrounding the hole 3, a transparent sheet 5 for blocking entrance of water from the hole 3 and allowing the state change of a water sinking confirmation seal 10 seen through from the surface thereof, and the water sinking confirmation seal 10 including a double side coated adhesive member 6 disposed at both ends of the transparent sheet 5 and a white plain paper 7, and the white plain paper 7 applied with red color printing 8 with a water-color ink at the center. The hole 3 is formed at a position not to be covered by another part mounted on the lower case 2, for example, above a holding member 1.

Figure 2:
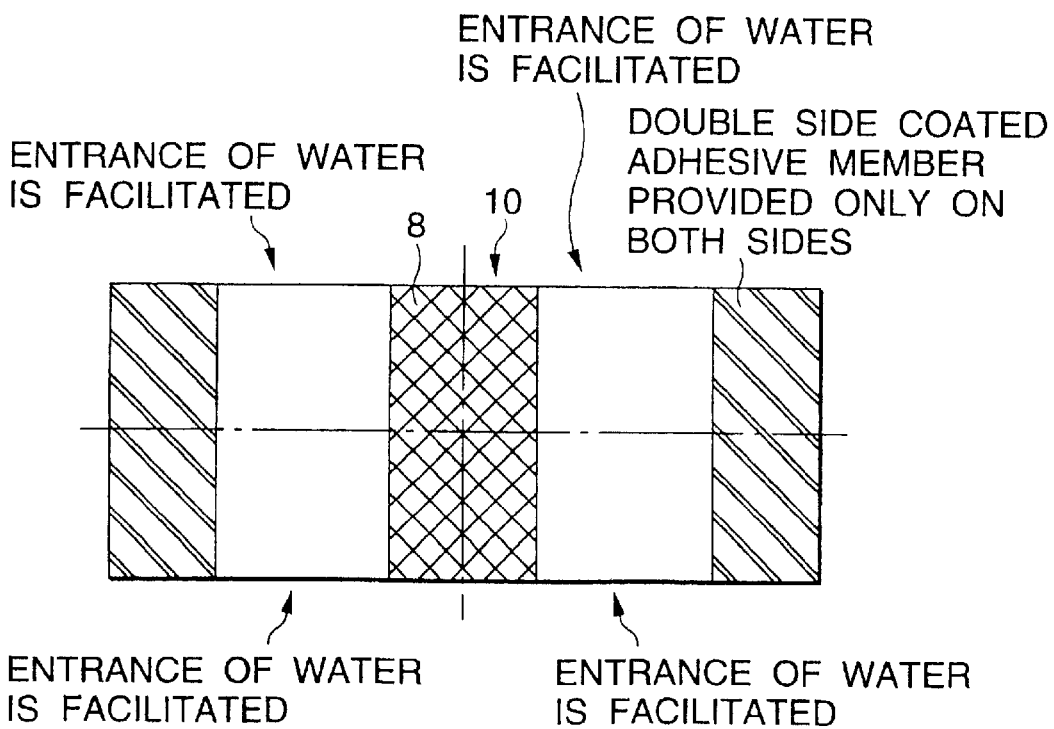
FIG. 2 is a plan view of a water sinking confirmation seal according to the embodiment of the invention.

FIG. 2 is a plan view of the water sinking confirmation seal 10, showing the state comprising the double side coated adhesive member 6 disposed below the transparent sheet 5, capable of bonding both sides at both end portions of the transparent sheet 5, and being applied with red color printing 8 with a water-color ink at the center. Moreover, as shown in the cross-sectional view of FIG. 1, since the double side coated adhesive member 6 is provided between the white plain paper 7 and the transparent sheet 5 so as to form a gap 9, consequently water can enter from the gap 9.

Figure 3:
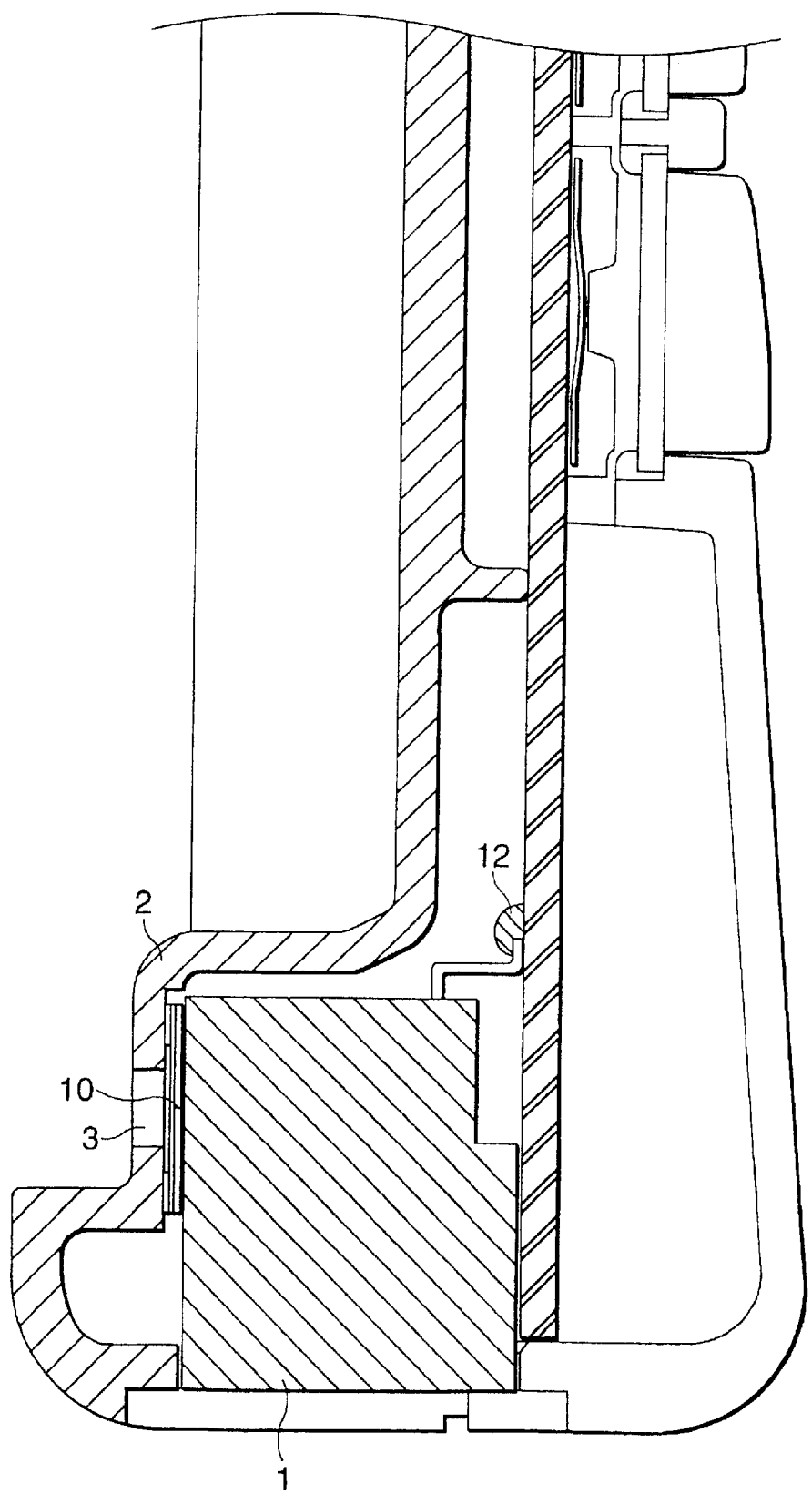
FIG. 3 is a cross-sectional view showing the configuration of the water sinking confirmation device according to the embodiment of the invention used in a portable terminal device.

FIG. 3 is a cross-sectional view of the configuration of the water sinking confirmation device used in a portable terminal device, such as a portable phone device. In FIG. 3, since the water sinking confirmation device is provided in the lower case 2 on the holding member (external connector) 1 attached on the lower part of the portable phone device, whether or not the portable terminal device, such as the portable phone device has been sunk in water can be judged only by exposing the lower case 2. Further, the water sinking confirmation seal 10 is attached to the lower case 2 at a position below a soldering portion 12 of the holding member 1 with the main body positioned upright.

Figure 4:
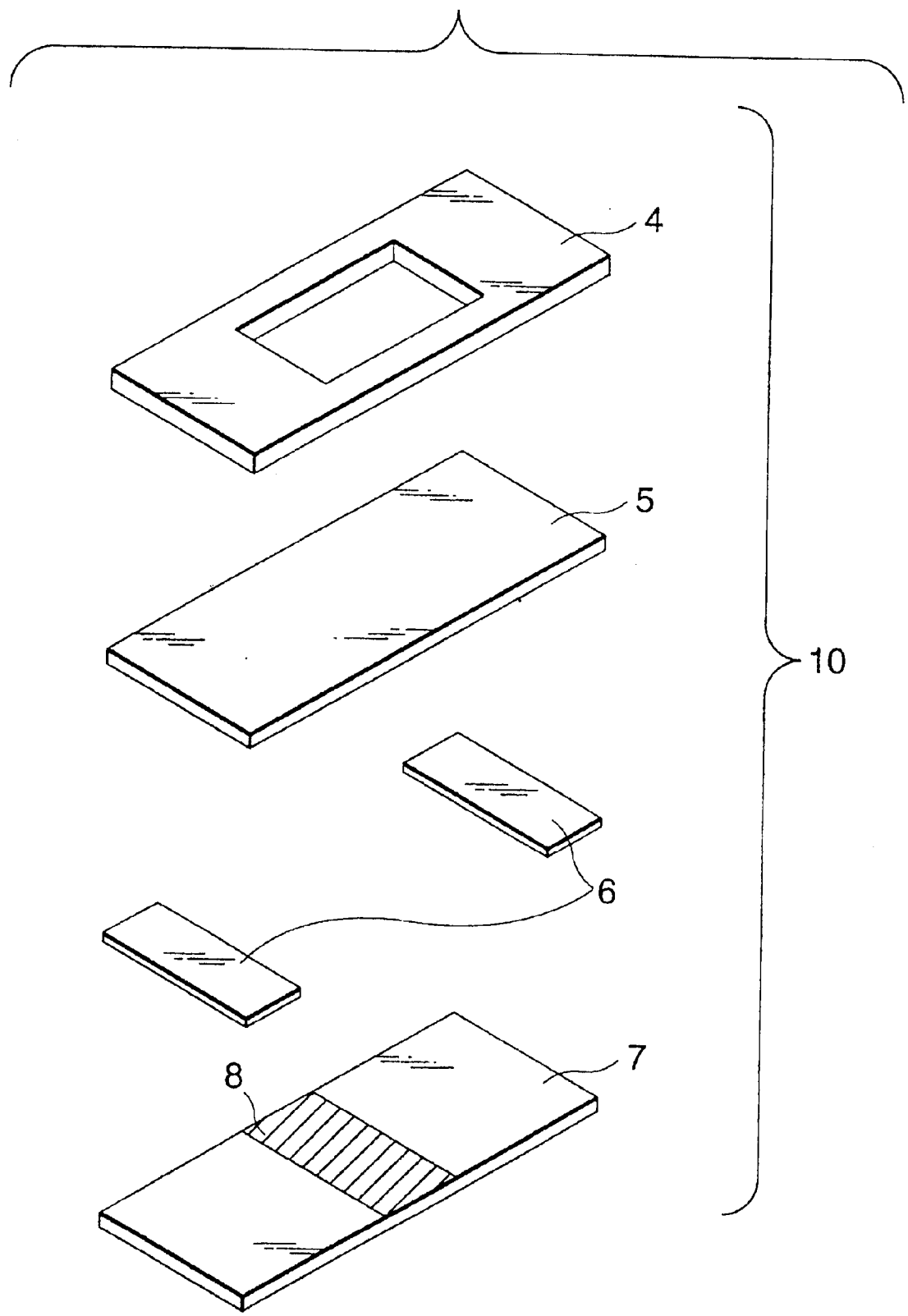
FIG. 4 is an exploded perspective view showing the order of assembling the water sinking confirmation device according to the embodiment of the invention.

FIG. 4 is an exploded perspective view showing the order of assembling the water sinking confirmation seal. In FIG. 4, the double side coated adhesive member 6 is placed and bonded on both ends of the white plain paper 7 applied with red color printing 8 with a water-color ink at the center. The transparent sheet 5 is placed and bonded on the double side coated adhesive member 6. Furthermore, the double side coated adhesive member 4 provided with a hole at the center is placed and bonded on the transparent sheet 5. The configuration shown in FIGS. 1 and 3 can be provided by bonding the water sinking confirmation seal thus assembled with the hole of the double side coated adhesive member 4 placed around the hole 3 of the lower case 2.

Therefore, since the hole 3 of the lower case 2 is surrounded by the double side coated adhesive member 4 and the transparent sheet 5 and thus water entering from the hole 3 of the lower case 2 can be blocked, the state of the water sinking confirmation seal 10 cannot be changed merely by moisture. Further, the water sinking confirmation seal 10 cannot be peeled off even if it is forced in from the hole 3 by mischief or the like.

Figure 5:
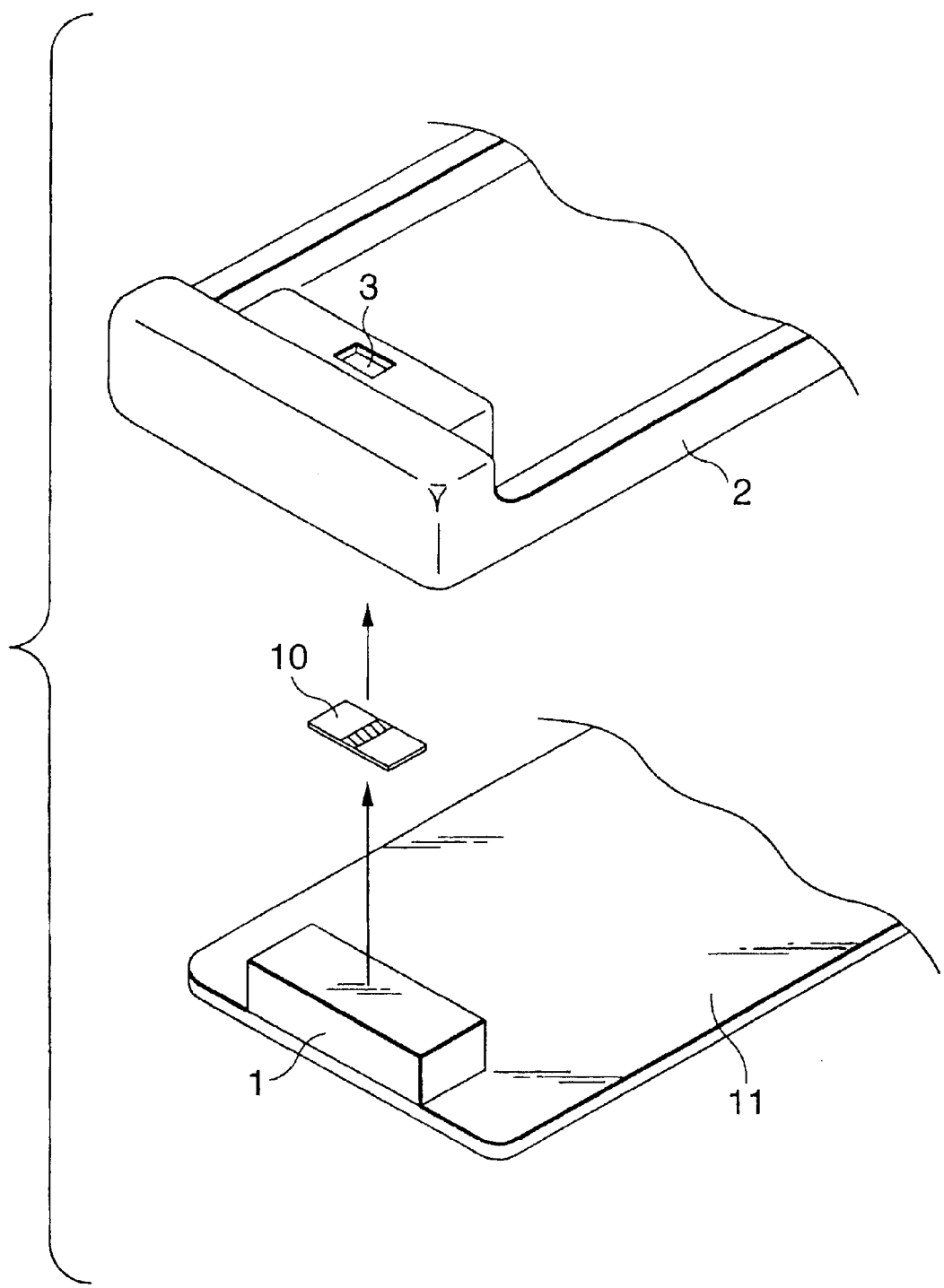
FIG. 5 is a perspective view for explaining the configuration of the invention, corresponding to a conventional configuration.
Figure 6:
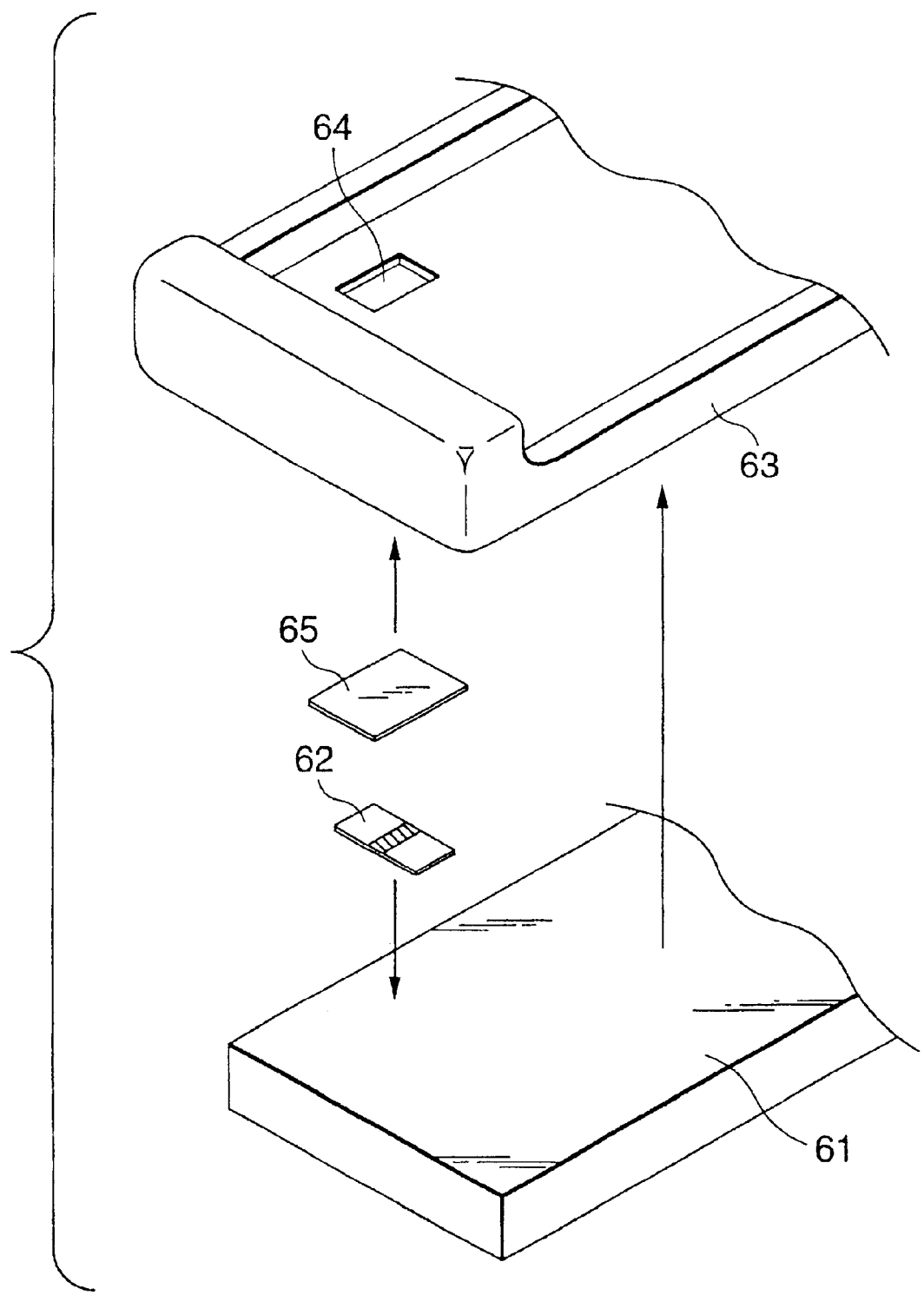
FIG. 6 is a perspective view showing the configuration of the conventional water sinking confirmation device.

FIG. 5 is a view for explaining the configuration of the invention, corresponding to the conventional configuration shown in FIG. 6. In FIG. 5, the water sinking confirmation device can be placed on the holding member 1 mounted on a predetermined position of the printed board 11 when the water sinking confirmation seal 10 is put on the lower case 2 at the hole 3 thereof from below.

As apparent from the above description, since the invention comprises a lower case provided with a hole for confirming water sinking, a double side coated adhesive member for bonding both sides, surrounding the hole, a transparent sheet allowing the state change of a water sinking confirmation seal later described seen through from the surface thereof, and the water sinking confirmation seal including a double side coated adhesive member disposed at both ends of the transparent sheet and a white plain paper later described, and the white plain paper applied with red color printing with a water-color ink at the center, the effect of enabling judgment on whether or not a portable terminal device or the like has been sunk in water only by seeing the lower case can be achieved.

What is claimed is:

1. A water sinking confirmation device comprising:
   a lower case provided with a hole for confirming water sinking;
   a double side coated adhesive member for bonding both sides surrounding the hole;
   a transparent sheet allowing a state change of a water sinking confirmation seal to be seen through the hole and the sheet from a surface thereof; and
   the water sinking confirmation seal including a second double side coated adhesive member disposed at both ends of the transparent sheet and a paper, the second double side coated adhesive member being disposed between the transparent sheet and the paper, the transparent sheet and the paper defining a gap therebetween approximately equal to the thickness of the second double side coated adhesive member, the gap between the transparent sheet and the paper facilitating entrance of water between the transparent sheet and the paper, and the paper applied with printing with a water-soluble ink, the state change being irreversible distortion of the printing after the case has been sunk in water.

2. The water sinking confirmation device according to claim 1, wherein the hole is formed at a position not to be covered by another part mounted on the lower case.

3. The water sinking confirmation device according to claim 1, wherein the transparent sheet blocks entrance of water from the hole according to the bond with the double side coated adhesive material for bonding both sides, surrounding the hole without the risk of peel-off even if it is forced in.

4. The water sinking confirmation device according to claim 1, wherein the water sinking confirmation seal is provided with a slight gap with respect to a holding member on a printed board.

5. The water sinking confirmation device according to claim 4, wherein the gap between the water sinking confirmation seal and the holding member on the printed board is narrower than a thickness of the water sinking confirmation seal.

6. The water sinking confirmation device according to claim 1, wherein the holding member serves also as a housing of an external connector.

7. The water sinking confirmation device according to claim 6, wherein the water sinking confirmation seal is attached to the lower case at a position below a soldering portion of the external connector with a main body positioned upright.

8. A portable terminal device comprising the water sinking confirmation device according to claim 1.

9. A portable phone device comprising the water sinking confirmation device according to claim 1.

10. A water sinking confirmation device according to claim 1, wherein the paper is white plain paper.

11. A water sinking confirmation device according to claim 1, wherein the water-soluble ink is red ink.

12. A water sinking confirmation device comprising:
    a case provided with a hole for confirming water sinking;
    a transparent sheet over the hole;
    an adhesive adhering the transparent sheet to the case;
    a water sinking confirmation seal comprising paper imprinted with a water-soluble ink; and
    an adhesive adhering the water sinking confirmation seal to the transparent sheet, a gap being defined between the water sinking confirmation seal and the transparent sheet, the gap being approximately equal to the thickness of the adhesive adhering the water sinking confirmation seal to the transparent sheet, the gap facilitating the entrance of water between the transparent sheet and the paper, whereby a state change of a water sinking confirmation seal can be seen through the hole and the sheet, the state change being that the water-soluble ink in the water sinking confirmation seal is irreversibly distorted after the case has been sunk in water.

13. A portable terminal device comprising the water sinking confirmation device according to claim 12.

14. A portable phone device comprising the water sinking confirmation device according to claim 12.

15. A water sinking confirmation device according to claim 12, wherein the water-soluble ink is imprinted over less than all of the surface of the paper.

16. A water sinking confirmation device according to claim 12, wherein the water-soluble ink forms a pattern on the paper.

17. A water sinking confirmation device according to claim 1, wherein the water-soluble ink is applied to less than all of the surface of the paper.

18. A water sinking confirmation device according to claim 1, wherein the water-soluble ink forms a pattern on the paper.

* * * * *